United States Patent [19]
Button et al.

[11] Patent Number: 5,786,584
[45] Date of Patent: Jul. 28, 1998

[54] VIAL AND CARTRIDGE READING DEVICE PROVIDING AUDIO FEEDBACK FOR A BLOOD GLUCOSE MONITORING SYSTEM

[75] Inventors: Timothy Hemenway Button, Indianapolis; Scott Forster Percy, Carmel, both of Ind.

[73] Assignee: Eli Lilly and Company, Indianapolis, Ind.

[21] Appl. No.: 699,766

[22] Filed: Aug. 20, 1996

[51] Int. Cl.[6] ............................................. G06K 7/10
[52] U.S. Cl. ..................... 235/462; 235/375; 235/385; 235/472; 235/486
[58] Field of Search .................. 235/462, 375, 385, 435, 439, 454, 470, 472, 486; 395/2.8; 128/920, 921; 422/64, 65, 66, 67, 102, 104; 250/234, 566, 568

[56] References Cited

U.S. PATENT DOCUMENTS

| | | | |
|---|---|---|---|
| 4,164,320 | 8/1979 | Irazoqui et al. | 235/375 |
| 4,476,381 | 10/1984 | Rubin | 235/375 |
| 4,622,457 | 11/1986 | Bradley et al. | 235/464 |
| 4,692,308 | 9/1987 | Riley et al. | 422/65 |
| 4,729,661 | 3/1988 | Bell | 356/437 |
| 4,760,245 | 7/1988 | Fukaya | 235/379 |
| 4,831,562 | 5/1989 | McIntosh et al. | 564/569 |
| 4,882,475 | 11/1989 | Miller et al. | 235/383 |
| 5,019,974 | 5/1991 | Beckers | 128/920 X |
| 5,088,056 | 2/1992 | McIntosh et al. | 364/569 |
| 5,091,634 | 2/1992 | Finch et al. | 235/375 |
| 5,291,399 | 3/1994 | Chaco | 235/375 X |
| 5,357,095 | 10/1994 | Weyrauch et al. | 235/375 X |
| 5,371,687 | 12/1994 | Holmes, II et al. | 364/514 |
| 5,401,110 | 3/1995 | Neeley | 235/375 X |
| 5,597,995 | 1/1997 | Williams et al. | 235/375 |
| 5,663,545 | 9/1997 | Marquiss | 275/375 |

*Primary Examiner*—Donald T. Hajec
*Assistant Examiner*—Michael G. Lee
*Attorney, Agent, or Firm*—Michael T. Bates; David E. Boone

[57] ABSTRACT

A device for reading the labeled contents of an insulin container and then providing an audible message informing the user of the labeled contents. The device includes a recessed surface, such as a cylindrical well, into which an insulin container is insertable by a vision impaired person. An optical scanner or reader reads a code furnished as part of the labeling on the inserted insulin container. A microcomputer compares the read code to known code patterns and a speech output is generated as to the type of insulin within the container. The speech output is broadcast over a speaker so as to be audible to a listener. The device may be integrated into a blood glucose sensor, or furnished in a unit that may assemble to an existing blood glucose sensor.

19 Claims, 15 Drawing Sheets

VIAL AND CARTRIDGE READING DEVICE PROVIDING AUDIO FEEDBACK FOR A BLOOD GLUCOSE MONITORING SYSTEM

CROSS REFERENCE TO RELATED APPLICATION

This application claims the benefit under 35 U.S.C. § 119(e) of United States Provisional Application Ser. No. 60/003,328, filed Sep. 6, 1995.

BACKGROUND OF THE INVENTION

The present invention pertains to blood glucose sensors or monitors for analyzing a blood droplet and outputting to the user a blood glucose reading, and, in particular, to a blood glucose sensor having an audio feedback.

Blood glucose sensors are well known in the art. Recently, sensors have been developed to include audio output to aid patients in monitoring their own glucose levels despite their vision loss. Such sensors have been called talking glucometers. One leading sensor is commercially available from Boehringer Mannheim Diagnostics, Inc., Indianapolis, Ind., under the trade name Accu-Chek® II Freedom System. In this device, a user deposits a drop of blood onto a test strip pad with the aid of a finger guide. The device optically senses the blood and outputs the audio instruction "Press the timer button." After the timer button has been pushed, a visual and audio blood glucose reading is communicated to the patient. The entire system is housed in a single unit. Another audio blood glucose monitoring system is commercially available from Home Diagnostics, Inc., Eatontown, N.J., under the trade name Diascan Partner. Like the Accu-Chek® II, this system is housed in a single unit and includes a voice module for providing messages on calibration and glucose readings.

Eli Lilly and Company ("Lilly"), a world leader in the production of insulin products, produces a number of different types of insulin to enable patients to better simulate their own natural glucose curves over the course of a day. For example, Lilly produces Humulin® R, Humulin® N, Humulin® L, Humulin® U, Humulin® 50/50, and Humulin® 70/30. A container of Lilly insulin typically includes a bar code on its label known as the "pharma code". This bar code is part of one type of internal security check which may be used in the manufacturing process to ensure that a specific label matches the contents of the container on which the label is affixed. Prior to the label being applied to a given container, the manufacturer scans the bar code to verify that an appropriate labeling is occurring.

Each of the Lilly insulin products is designed for a particular glucose level and for a particular duration. Often, a patient will inject himself/herself with one insulin product in the morning and a different insulin product in the afternoon and/or evening. Serious adverse medical consequences could occur if a patient mistakenly grabs the wrong insulin container and injects himself/herself with the wrong insulin product (e.g. Humulin® R instead of Humulin® U). Accordingly, it is important that the patient choose the correct insulin container for use at a given time.

The selection of the correct insulin container is generally not a problem for those individuals having good eyesight and who can easily read the label on the container. However, for those individuals with limited or no vision, a greater risk exists that a misreading or a failure to read the label on the container will occur, which in turn may result in an inadvertent selection of a wrong container. Because impaired vision is often a result of diabetes, this problem can be significant.

Thus, it is desired to provide a device which aids the vision impaired patient in choosing the correct insulin container for insulin injection.

SUMMARY OF THE INVENTION

The present invention provides a voice synthesizer device allowing a visually impaired person or diabetic to independently determine the contents of insulin containers. The device first identifies the labeled contents of an insulin container, and then generates an audible message to inform the user of the contents. The insulin container includes a readable code, such as a bar code, on its label. When the bar code is read by an optical scanner in the device, a voice synthesizer coupled to a speaker in the device produces an audible message to a user as to the contents of the insulin container. The device may be integrated into a blood glucose sensor, or provided in a unit that assembles to an existing blood glucose sensor.

In one form thereof, the present invention provides a device for identifying a labeled content of a medication container including a body with a portion shaped to accommodate a container containing a medication, a reader arranged to read a medication identifying code on the container when the container is positioned at the body portion, a controller within the body and circuited to the reader to receive a signal from the reader corresponding to the read code, wherein the controller compares the signal to stored data, a voice synthesizer for generating a speech pattern identifying the medication in the container responsive to the controller comparing the signal and stored data, and a speaker for broadcasting the speech pattern to provide an audible message to a user of the device.

In another form thereof, the present invention provides an insulin label reading device including a body, which is either configured as an adaptor into which a separate portable blood glucose sensor removably inserts or configured as a housing into which a portable blood glucose sensor is integrated, means, within the body, for reading an insulin identifying code on an insulin container, and means, circuited to the code reading means, for providing an audible message to a user identifying a type of insulin labeled by the code as within the container.

In still another form thereof, the present invention provides the combination of a medication container which includes a code arranged on a portion of an exterior container surface, and a device for identifying a labeled content of the medication container. The device includes a body including a portion complementarily shaped to the medication container, a code reader arranged to read the code on the container when the container is positioned at the portion, a controller within the body and circuited to the code reader to receive a signal from the code reader corresponding to the read code, wherein the controller compares the signal to stored data, a voice synthesizer for generating a speech pattern identifying the medication in the container responsive to the controller comparing the signal and stored data, and a speaker for broadcasting the speech pattern to provide an audible message to a user of the device.

One advantage of the present invention is that an audible message as to the labeled contents of a medication container is provided.

Another advantage of the present invention is that its user-friendly design allows its use by a person with impaired vision to independently determine the labeled contents of a medication container.

BRIEF DESCRIPTION OF THE DRAWINGS

The above mentioned and other advantages and objects of this invention, and the manner of attaining them, will become more apparent and the invention itself will be better understood by reference to the following description of embodiments of the invention taken in conjunction with the accompanying drawings, wherein.

Figure 1:
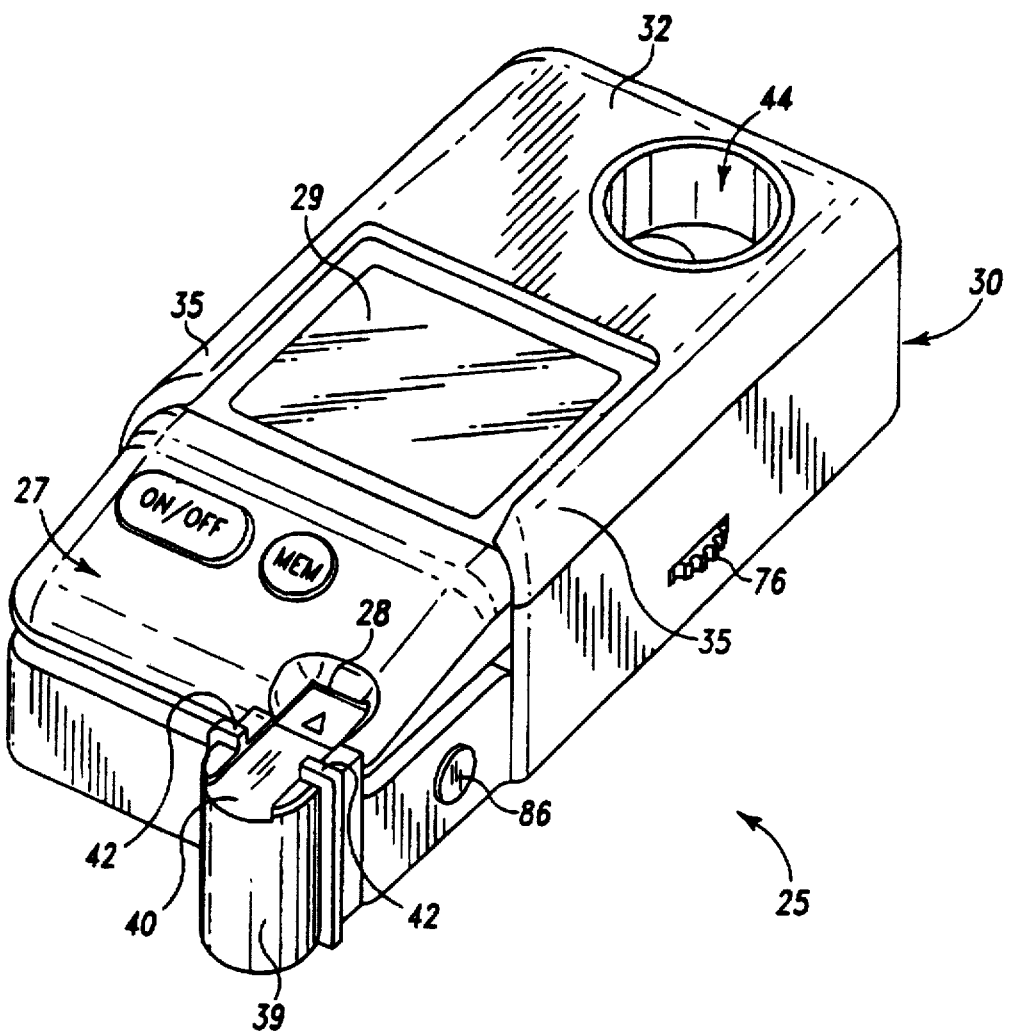
FIG. 1 is a perspective view of a first embodiment of the present invention in which a blood glucose monitor is removably housed within a base unit including a vial and cartridge reader of the present invention.

Corresponding reference characters indicate corresponding parts throughout the several views. Although the drawings represent multiple embodiments of the invention, the drawings are not necessarily to scale and certain features may be exaggerated or omitted in selected drawings in order to better illustrate and explain the present invention.

DESCRIPTION OF THE PREFERRED EMBODIMENTS

Referring now to FIG. 1, there is shown a front perspective view of a first embodiment of a blood glucose monitoring system of the present invention. The system, which is generally designated 25, includes a blood glucose sensor or monitor 27 with a visual display 29 mounted within a separate housing or base unit, generally indicated at 30. In this system embodiment, base unit 30 serves as a voice synthesizer adaptor which furnishes an existing sensor product with the inventive features of first identifying the labeled contents of an insulin container and then broadcasting an audible message to a user as to the identity of the contents. The configuration of sensor 27 shown in FIG. 1 and in the additional embodiments conforms to the Accu-Chek® Advantage™ blood glucose monitor, which is commercially available from Boehringer Mannheim Corporation of Ind., Indiana. Except as further explained below, additional detail regarding the Advantage™ type monitor and the associated test strips are not necessary for an understanding of the present invention, and therefore are omitted herein. Such detail can be found in the User's Manual for the Advantage™ type monitor and U.S. Pat. Nos. 4,963,814, 4,999,582, 4,999,632, and 5,243,516, which are all incorporated herein by reference.

It will be appreciated that with appropriate modification, base unit 30 can be adapted to function with other types of existing blood glucose monitors.

Alternatively, rather than being provided within an accessory or separate component which retrofits existing monitors as shown, the inventive features may be integrated into the housing and internal circuitry or workings of a blood glucose monitor product, including one having other audio or visual feedback designs, within the scope of the invention. Moreover, the explanation herein with reference to a blood glucose monitoring system is illustrative and not limiting, as the inventive features may find beneficial application in identifying other types of medications within containers.

Figure 2:
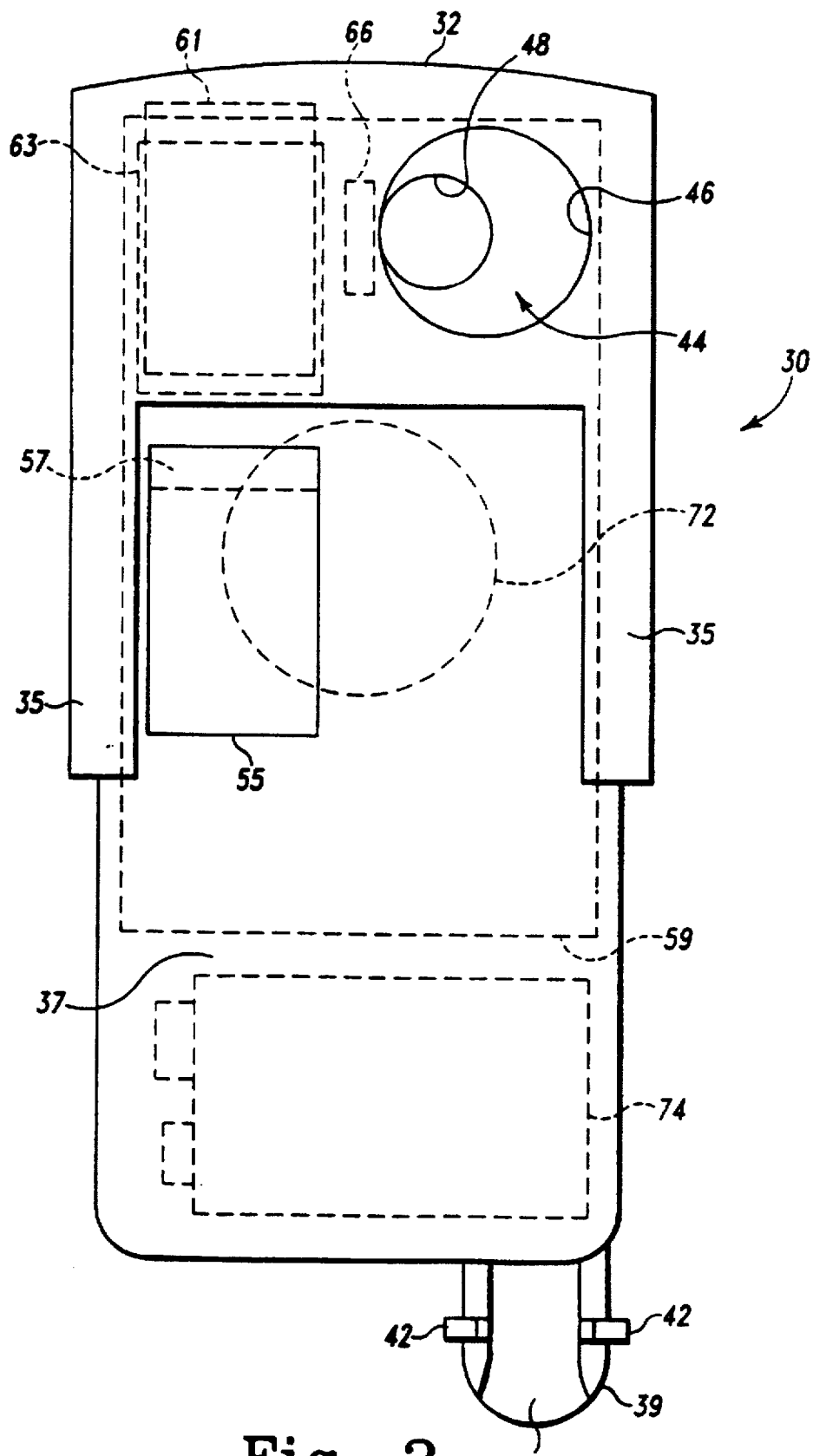
FIG. 2 is a plan view of the embodiment of FIG. 1 with the monitor shown removed, and wherein selected internal components contributing to the container reading and audio output functions are diagrammatically shown in dashed lines.
Figure 3:
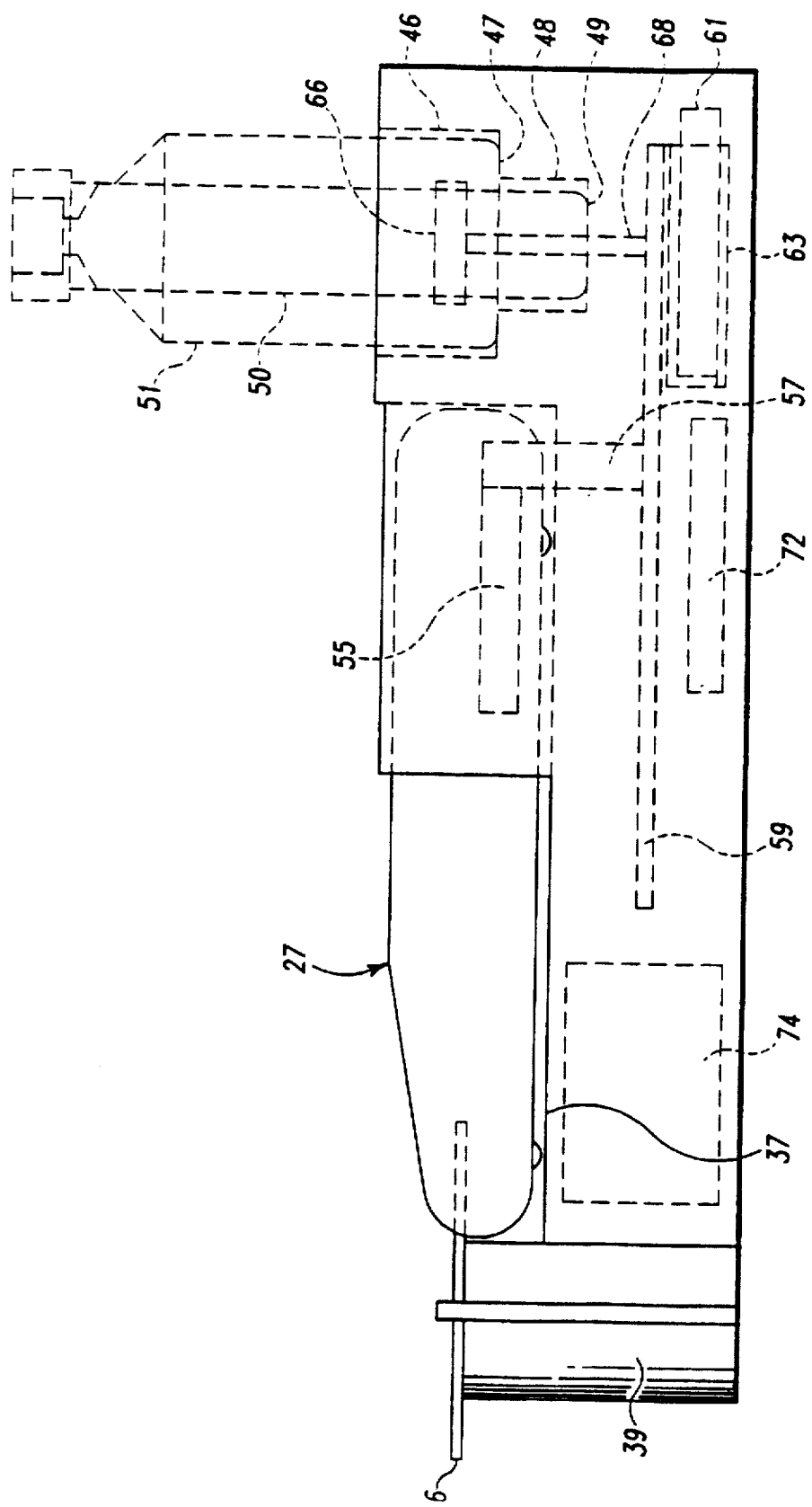
FIG. 3 is a diagrammatic side view of the embodiment of FIG. 1, wherein select portions of the invention are shown in dashed lines.

Blood glucose monitoring system 25 will be further described with additional reference to FIGS. 2 and 3. FIG. 2 is a plan view of system 25 with monitor 27 removed from base unit 30 for purposes of illustration, and wherein selected components of the internal workings of base unit 30 are diagrammatically shown in dashed lines. FIG. 3 is a diagrammatic side view of system 25 from FIG. 1 with selected components again shown in dashed lines, and with the outlines of two different types of insulin containers shown in dashed lines inserted within base unit 30 in bar code scannable arrangements.

Base unit 30 includes a main housing or body 32 made of a washable, durable plastic material which may be formed in the shown shape from mating or secured together parts. Rubber standoffs (not shown) on the base unit bottom surface provide stability during use. Two forwardly extending flanges 35 of body 32 each have an interior surface contoured to the sides of monitor 27 and serve to retain monitor 27 on body platform 37. A guide member 39 is detachably mounted to the forward end of body 32. As shown in FIG. 3, the upper portion of guide member 39 projects above the height of platform 37 and prevents monitor 27 from sliding out from an installed or inserted position between flanges 35.

Guide member 39 provides tactile guidance to aid a vision impaired user in properly inserting and then dosing a test strip by feel. Guide member 39 includes a channel 40 sized and configured to guide a test strip 26 (see FIG. 3) during its insertion into blood sample insert port 28 of monitor 27. When test strip 26 is properly inserted into port 28, ridges 42 align with an opening in the test strip whereat a droplet of blood is to be applied. Guide member 39 may be removably attached to body 32 in a variety of ways. For example, guide member 39 may include a downwardly opening hollow, defined by a keyed interior surface, which fits over a complementarily designed lip forwardly projecting from body 32. Guide member 39 and the projecting body lip may be provided with mating latching elements, such as a rod and a cooperating bore, to secure guide member 39 to body 32 to limit occasions of inadvertent disassembly. Other guide member shapes may be provided in addition to the alternate configurations shown herein. For example, the guide member could define a cavity into which the tip of a user's finger fits during application of the blood droplet.

Along its top surface, body 32 includes a recessed surface, generally designated 44, into which insulin containers may be separately introduced for a reading of their labeling. As better shown in FIGS. 2 and 3, recessed surface 44 defines a first cylindrical concavity 46 and a second cylindrical concavity 48. Concavity 48 opens into concavity 46 and extends deeper into body 32 than concavity 46. Concavities 46, 48 are shown as well-shaped cavities or "wells" particularly sized and shaped to accommodate specific types of insulin containers.

Insulin is conventionally available to users in two different types of containers. One type is a vial that usually contains ten milliliters of liquid insulin. A single-use syringe includes a needle that pierces the rubber stopper at the top of the vial to draw up the desired amount of insulin. Another type of container is a cartridge, primarily designed for use with multiple dose syringes.

Cartridges for insulin are often available in two sizes, namely three milliliters and one and one-half milliliters. Both vials and cartridges are conventionally made of glass.

Figure 4:
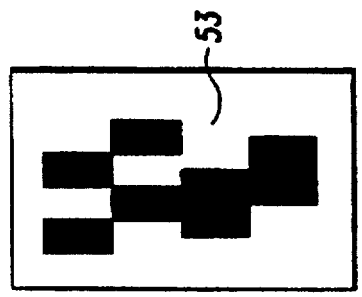
FIG. 4 is a diagrammatic front view illustrating the placement of bar codes on different types of insulin containers.

Cylindrical concavity 48 has a diameter sized to insertably receive the cylindrical end of a three milliliter insulin cartridge shown in dashed lines at 50. Cylindrical concavity 46 is sized to receive the bottom cylindrical end of a ten milliliter insulin vial shown in dashed lines at 51. Base unit 30 naturally may be designed to only accommodate one type of container, such as vials which have a larger circumference upon which coding may be more readily positioned. According to the present invention, the label which is affixed to each insulin container is provided with a readable code that is used in identifying the contents of the insulin container. As abstractly shown in FIG. 4, which is a front view showing the outlines of cartridge 50 and vial 51 as relatively positioned when fully inserted into their respective concave wells 48, 46, a bar code 53 is located on the cylindrical periphery of each of the containers at a height indicated in dashed lines. Bar code 53 will normally be a preprinted part of the overall label artwork and be in addition to the pharma code. Bar code 53 may alternatively be separate from the overall label and separately affixed or otherwise incorporated into the container. For different containers, bar codes 53 are positioned at different heights from the container bottoms in conjunction with the different well depths. As shown in FIG. 4, this positioning technique allows the bar codes of both vials and cartridges to be read by a common reader or scanner, which is indicated at 66 and described further below.

The type of code used for bar code 53 may be selected by one of ordinary skill in the art. A suitable bar code for use with a four-channel bi-directional bar code reader includes black bars on a white background. The black bars are up to 90% less reflective than the white backdrop. The bar code is bi-directional in that it is readable for either direction of container rotation as described below. The top channel of the bar code contains four bits of information identifying the type of insulin. The second channel is the inverse of the top channel and is vertically aligned with the top channel. The lower two channels are quadrature channels. Each of these channels contains one bar that is two bits wide and the vertical alignment of these channels relative to the data channels is such that one edge of a bar from one of the channels is aligned with the middle of the bar in the data channel. The output of the quadrature channels produces a gray code that changes at the center of the data bits.

Figure 5:
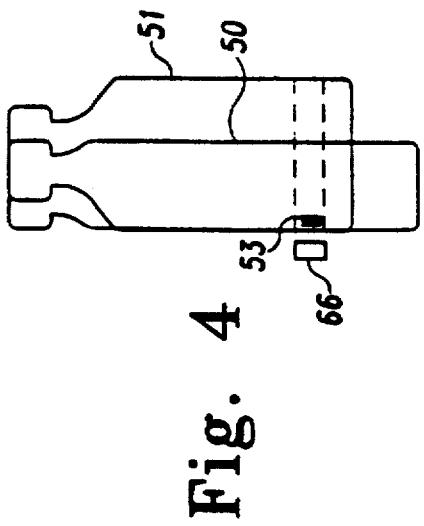
FIG. 5 is a front view of an example of a bar code for a container label.

For a ten milliliter vial, FIG. 5 is an example of how a particular pattern, namely 0101, appears on the white background of the vial. The bar code includes at least four bits in the top two channels, and is at least approximately 0.160 inch wide (four bits at 0.040 inch per bit). The bar channel height is at least approximately 0.74 inch (four channels at 0.185 inch per channel). The minimum position of the bar code is approximately 0.230 inch from the bottom of the ten milliliter vial.

Referring again to FIGS. 2 and 3, connector plug 55 including circuit pins is cantilevered above base platform 37. Plug 55 is circuited to the internal electronic circuitry or microcomputer of base unit 30 via a connector indicated at 57. This microcomputer or internal circuitry, which controls the operations of base unit 30, is generally referenced as 59 and is abstractly shown in the form of a printed circuit board for purposes of illustration, but may be alternatively configured within the scope of the present invention. When monitor 27 is mounted to base unit 30, plug 55 inserts into a code key slot or compartment within the back of monitor 27 to provide an electrical interface between the microcircuitry of monitor 27 and base unit 30. In an Advantage™ type monitor such as 27, the code key slot normally receives a code key or chip included with each container of test strips purchased by the user. The code key calibrates the monitor for use with a particular set of test strips. In the embodiment of FIG. 1, such a code key is shown at 61 operationally installed in a ROM key port 63 within body 32 that is circuited with internal circuitry 59. Code key 61 is manually, slidably insertable into port 63 and removable therefrom through an opening (not shown) in the rear and bottom surface of body 32 that is configured similar to the corresponding housing opening of the Advantage™ type monitor.

Insulin bar code reader or scanner 66 is positioned at a height within recessed surface 44 at which bar code 53 will be located when either container 51 or 50 is fully inserted into its respective well. Bottom or stop surfaces 47 and 49, which abut the inserted container ends, are arranged at a longitudinal distance from scanner 66 equal to the distance between the bar code and container bottom such that this bar code positioning is achieved. Scanner 66 faces radially inward and ports through recessed surface 44 so as to open into the container wells to read bar code 53. Scanner 66 is circuited with internal circuitry 59 by a connector 68 through which electrical power and signals are communicated.

A suitable scanner or bar code reader 66 is an optical sensor employing IR LEDs and sensors adapted to read the black on white bar code. Other types of cooperating codes/readers may alternatively be employed. As used herein, the term codes encompasses more than merely written or printed indicia such as those having no apparent meaning to the untrained eye, and includes comprehensible markings as well as elements that mechanically or otherwise engage a complementarily structured "reader" to furnish input as to the particular container contents.

Internal circuitry 59 includes a speech controller or voice synthesizer circuitry, which may be supplied as an integrated computer chip connected to a circuit board. Speaker 72 is circuited to voice synthesizer 59 with not shown conductors and broadcasts the speech pattern output by voice synthesizer 59 to convey an audible message to a user. Not shown apertures provided through the portion of the bottom panel of base unit body 32 covering speaker 72 facilitate sound transmission.

A power supply for base unit 30 is supplied independent of the normal battery for monitor 27. A battery 74, such as a nine volt alkaline battery, fits within an internal compartment provided in body 32 and is electrically connected to circuitry 59 with not shown conductors to provide suitable electrical energy to base unit 30. Rather than using battery power, base unit 30 may be plugged into an AC current source through the use of a jack (not shown) provided on body 32.

The overall structure and operation of blood glucose monitoring system 25 will be further understood in view of the following explanation of its utilization. Base unit 30 may be operated to identify container contents when monitor 27 is not provided, or when monitor 27 is installed and used for its blood glucose testing capabilities. Base unit 30 is turned on by manually rotating combination ondial 76 shown in FIG. 1. The volume level of speaker 72 can be controlled by the degree of rotatcon of dial 76 from its off position as is conventional. If monitor 27 is installed as shown in FIG. 1, turning on base unit 30 automatically turns on monitor 27. The microcomputer with voice synthesizer 59 and speaker 72 may be programmed to cooperate with monitor 27 to supply speech output appropriate for the normal operations of monitor 27. For example, prompts suitable to help a vision impaired user perform a blood glucose test with monitor 27 and test strip 26 may be broadcast. In addition, all available Advantage™ type monitor function indicators, error messages, control results, test results, and memory results with corresponding date and time may be broadcast.

To utilize the insulin container contents identifying feature, a user inserts an insulin container into either well 46 or 48 as appropriate. It will be recognized that the well-shaped recess guides even the most visually impaired user in properly inserting by feel the container to be read by scanner 66. To facilitate explanation, the following explanation will assume a labeled vial is the insulin container to be read. In some circumstances, the insertion into well 46 may be in response to an audible, instructional prompt of "insert vial" broadcast by speaker 72 in response to a command by microcomputer 59. Because a sight impaired user will typically be unable to assure a proper alignment of bar code 53 with scanner 66, the invention is designed such that the rotational orientation of insulin vial 51 at the time of its insertion does not compromise the operation of the system.

After the vial insertion is sensed, such as by an additional microswitch (not shown) at the base of well 46, the voice synthesizer of internal circuitry 59 then generates a speech output which is broadcast through speaker 72 as "rotate vial". In response to this prompt, a user rotates or spins vial 51 to effect bar code reading. The user may rotate vial 51 within well 46 in either direction and still obtain a proper insulin identification due to the bi-directional aspect of bar code 53.

Figure 6:
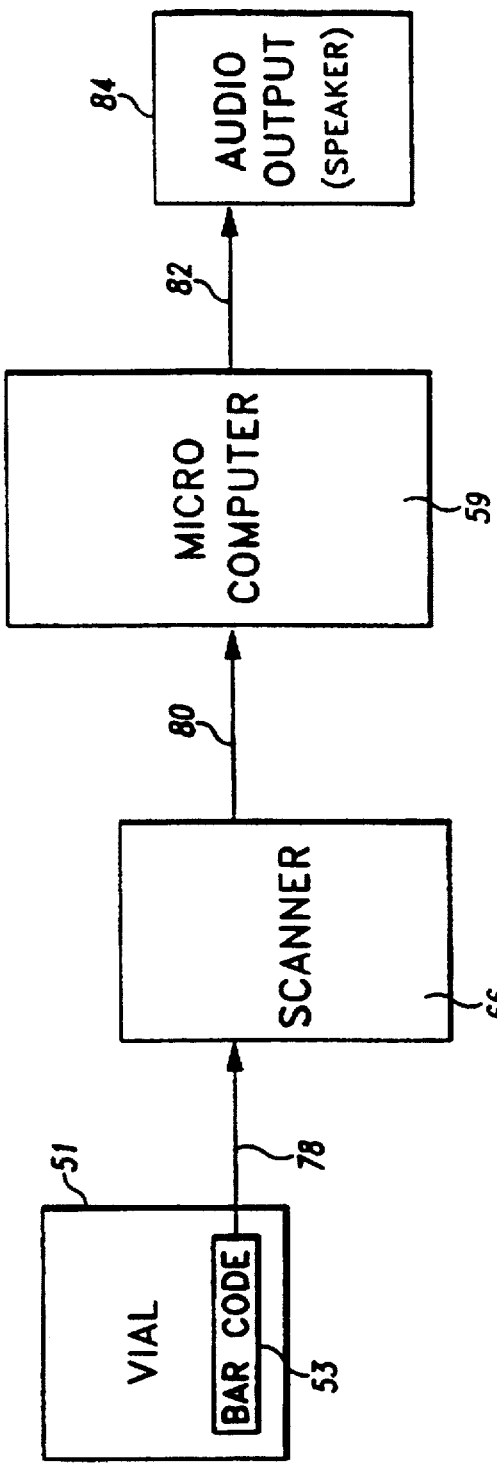
FIG. 6 is a general block diagram of the code scanning and audio output functions of the present invention.

With additional reference to the schematic of FIG. 6, during vial rotation, scanner 66 reads bar code 53 in a process represented at 78. Responsive to its reading bar code 53, scanner 66 then outputs a signal at 80 corresponding to the read code. Signal 80 is transmitted through connector 68 and reaches microcomputer 59, which compares inputted signal 80 to a number of separate, stored patterns associated with various types of insulin. For example, sixteen unique patterns, each of which corresponds to a different one of Lilly's insulin products, may be stored. These reference patterns will typically be stored in and retrieved from code key 61, but may alternatively be stored in and accessed from a memory module or circuit provided in internal circuitry 59. After the inputted signal 80 is compared to the known patterns, the voice synthesizer within microcomputer 59 produces a speech output signal 82 transmitted to speaker 72, which broadcasts the signal as an audio message or output 84 to be heard by the user. If inputted signal 80 was matched to one of the recognized, stored patterns, speech output signal 82 causes speaker 72 to broadcast an audible message which informs the user as to the type of insulin which the label claims to be in vial 51. If no match is found, speech output signal 82 causes the message broadcast by speaker 72 to be that a valid bar code was not found and that the insulin vial should be re-inserted. If a user misses the message broadcast through speaker 72, repeat button 86 (See FIG. 1) may be pressed to automatically replay the last message broadcast through speaker 72.

In addition to the numerous system features shown and described with reference to the embodiment of FIG. 1, additional features may be provided to system 25 within the scope of the present invention. For example, base unit 30 may be provided with a button which accesses the memory of monitor 27, and which can be used to program the monitor. Base unit 30 may include a button to change the gender of the voice announcing the outputted messages, and a button to change the language of the outputted message, for example from English to Spanish. In addition to the insulin type, the bar code 53 and overall programming and memory of base unit 30 could be modified to audibly communicate additional information, such as the insulin expiration date. A headphone jack, as well as an automatic turn-off feature after passage of a finite period of system inactivity, may also be furnished. In conjunction with bar code reader 66, a calibration device may be provided with a fixed predetermined bar code for use to insure the functionality of reader 66.

Figure 7:
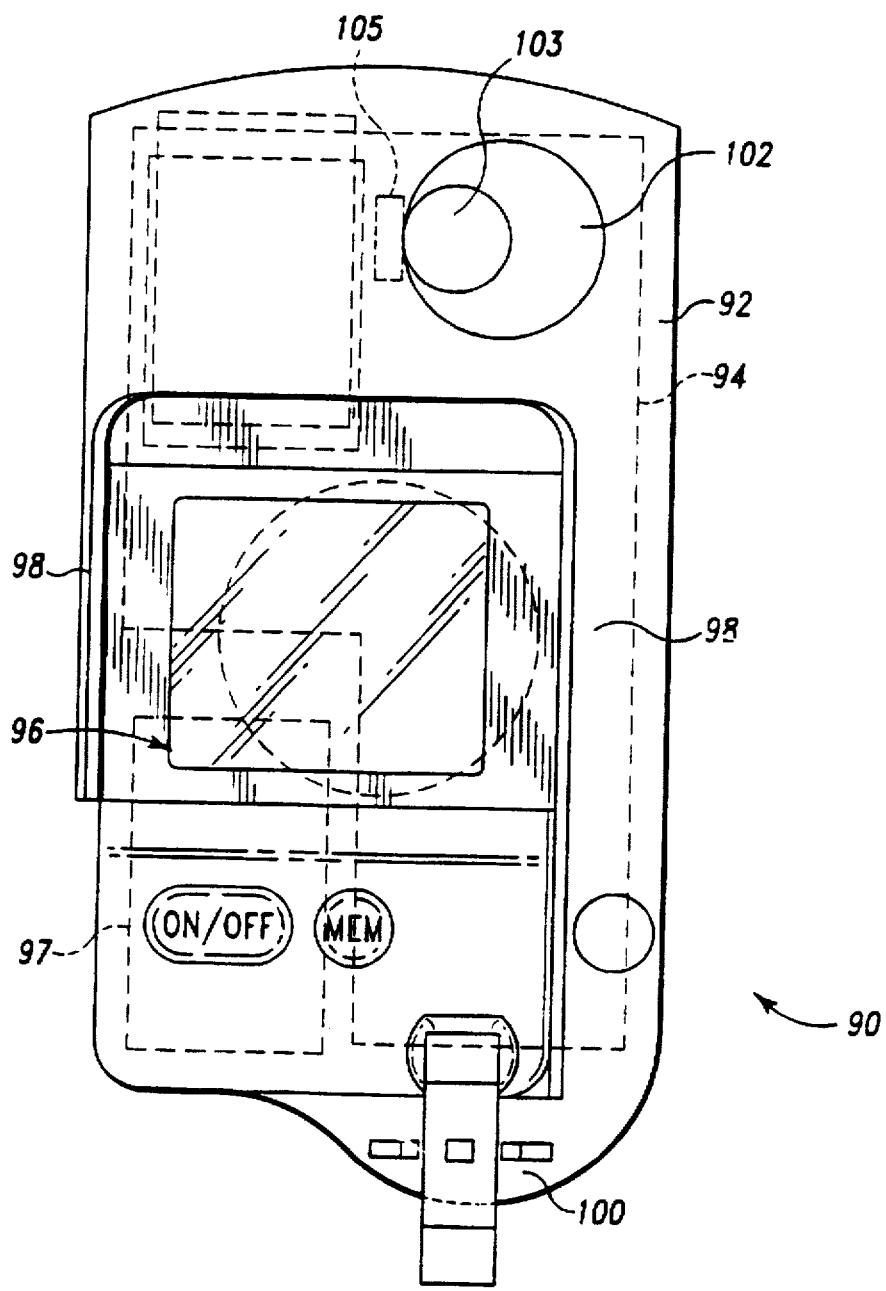
FIG. 7 is a plan view of a second embodiment of a blood glucose monitoring system of the present invention.

Referring now to FIG. 7, there is shown a plan view of a second embodiment of a blood glucose monitoring system 90 of the present invention. System 90 and the additional embodiments shown and described below are conceptually similar in numerous respects to the embodiment of FIG. 1, and each of these embodiments includes the label reading and audible label identifying features described in greater detail above with reference to system 25. Therefore, further description of these alternate embodiments primarily focuses on differences between the systems and additional detail pertinent to a further understanding of system 25. As shown in dashed lines in FIG. 7, system 90 includes an L-shaped printed circuit board 94, with the notch forming the "L" providing space within housing or body 92 for battery 97. An Advantage™ type blood glucose monitor 96 is laterally off-set along the top surface of body 92 and held within the base unit by flanking flanges 98 and guide member 100. As with the embodiment of FIG. 1, insulin vials and cartridges are insertably received within well shaped receptacles 102 and 103, respectively, such that the insulin container bar codes can be scanned by reader 105 during container rotation.

Figure 8:
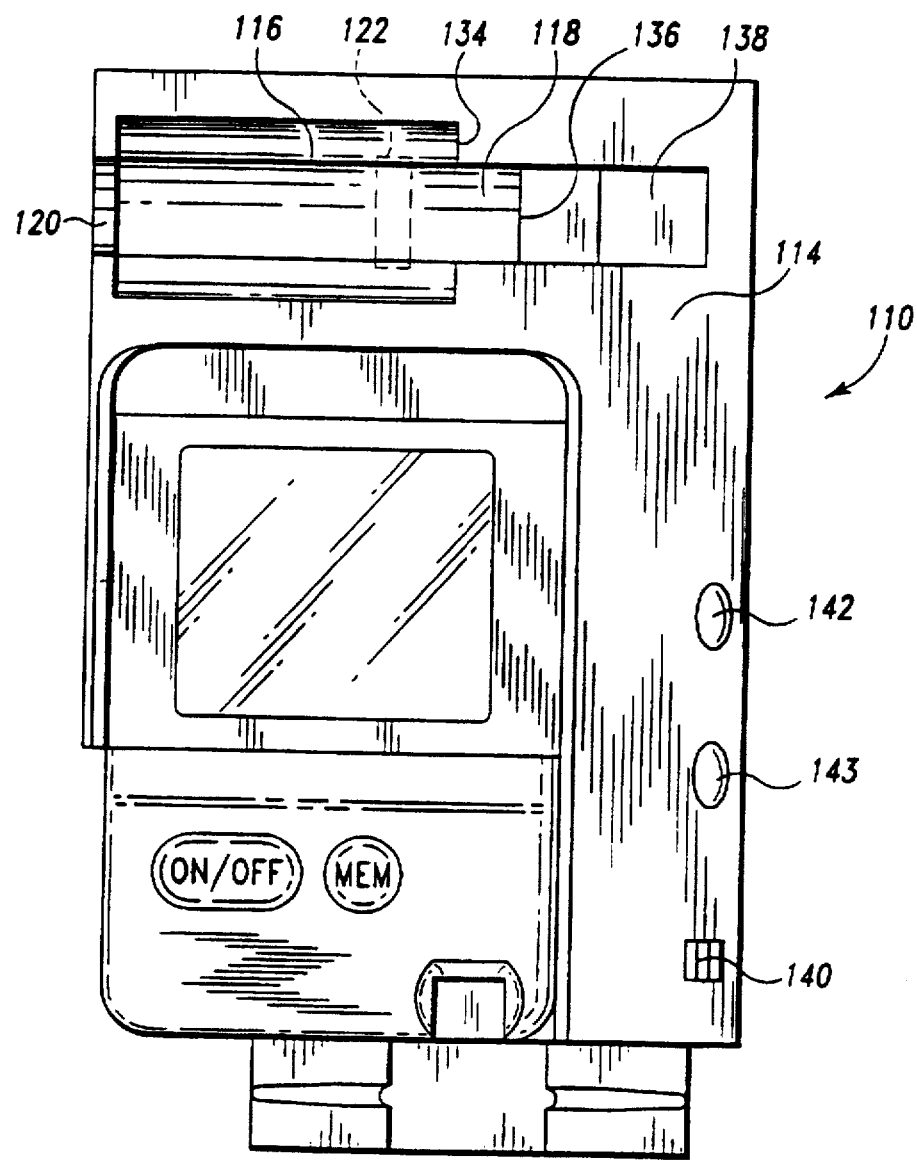
FIG. 8 is a plan view of a third embodiment of a blood glucose monitoring system of the present invention.
Figure 9:
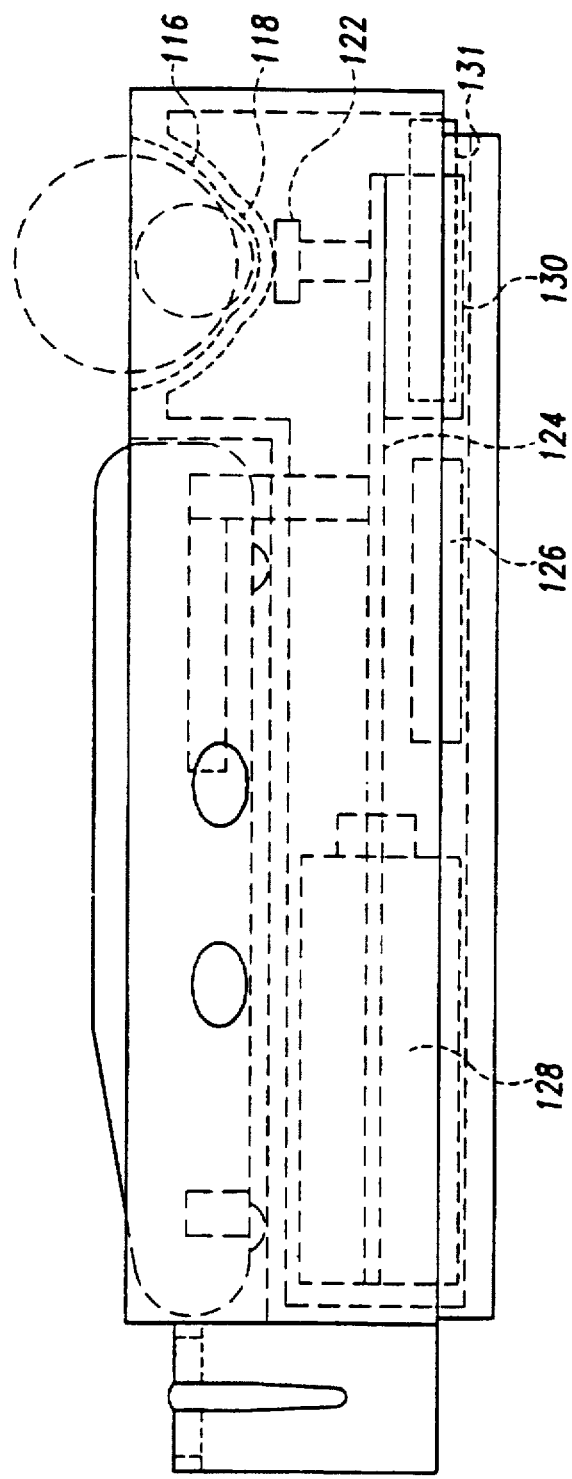
FIG. 9 is a diagrammatic side view of the system of FIG. 8, wherein some of the internal components and inserted containers are diagrammatically shown in dashed lines.

Referring now to FIGS. 8 and 9, a third embodiment of a blood glucose monitoring system 110 of the present invention is illustrated. FIG. 8 is a top view of system 110. FIG. 9 is a diagrammatic side view of system 110, wherein selected internal components of the system are diagrammatically shown in dashed lines and wherein a vial and cartridge are shown in dashed lines positioned within the system in bar code readable arrangements. The top surface of base unit body 114 includes a curved recess shaped to accommodate both standard size insulin vials and cartridges placed therein. The curved recess includes a vial receiving recess portion 116 which is generally in the shape of a half or partial cylindrical surface. Longitudinally extending along the central segment of vial recess 116 is a smaller diameter, cartridge receiving recess 118. Cartridge recess 118 extends into body 114 both deeper and further laterally, or to the right in FIG. 8, than does vial recess 116. The neck or top portions of the insulin containers extend through a notch 120 provided in the side face of body 114. Recesses 116, 118 are contoured to allow different sized cylindrical containers to be inserted or placed on their respective sides within body 114. When a user rotates a container within the body recess in either a clockwise or counter-clockwise direction from the perspective of a FIG. 9 viewer, the container bar code passes before an upwardly facing scanner 122, in communication with a microcomputer 124, which is circuited with speaker 126, battery 128, and code key 131 by way of key port 130 as described with reference to system 25. The end of vial recess 116 is defined by a partial annular stop surface or shoulder 134, and cartridge recess 118 includes a stop shoulder 136, which ensure that the bar codes on the containers are properly located above scanner 122 upon the blind insertion of the containers. In system 110, a power switch 138 is provided separate from volume switch 140. A separate language button 142 and repeat button 143 are also shown.

Figure 10:
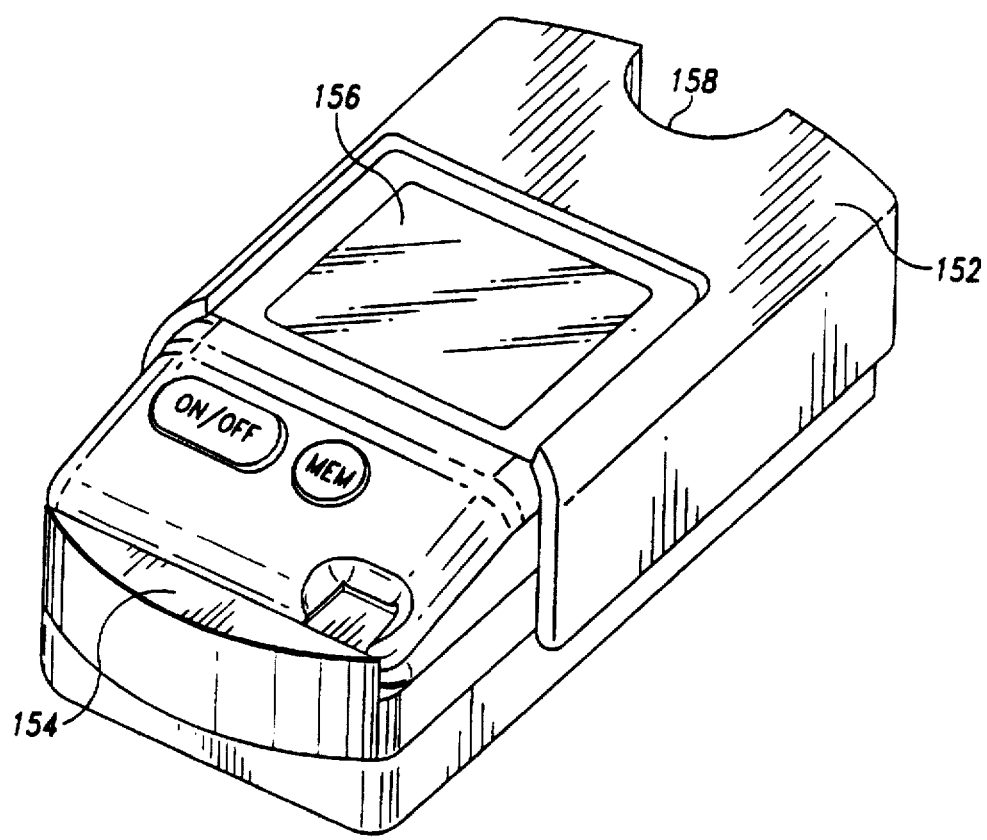
FIG. 10 is a front perspective view of a fourth embodiment of a blood glucose monitoring system of the present invention.
Figure 11:
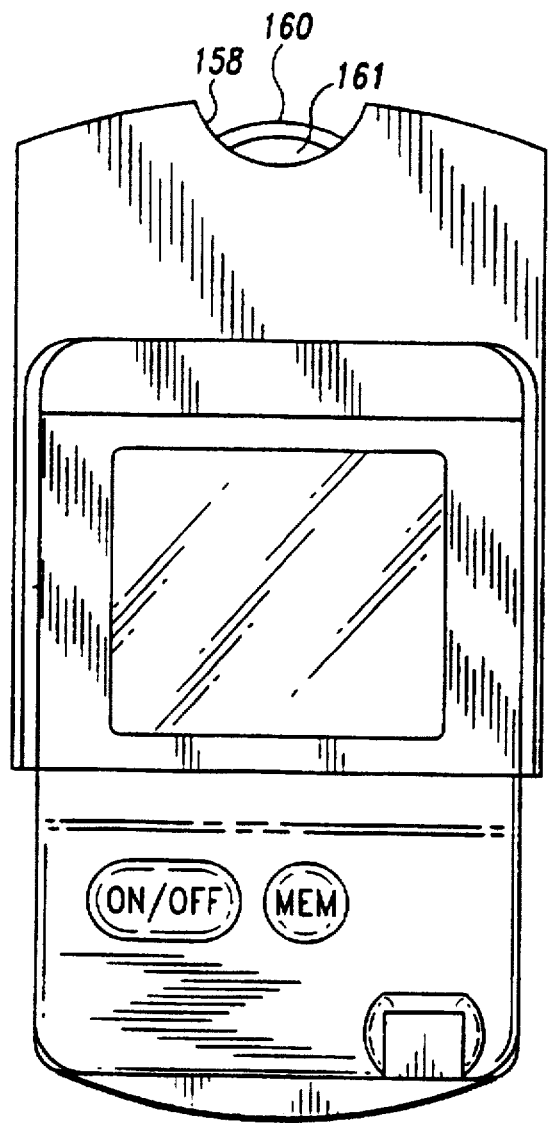
FIG. 11 is a top view of the system of FIG. 10.

Referring now to FIGS. 10 and 11, shown are a front perspective view and a top view of a fourth embodiment of a blood glucose monitoring system of the present invention. This system includes a base unit body 152 and a front lip element 154 that holds Advantage™ type monitor 156 within the base unit. The back edge or surface of body 152 includes a vertically aligned, partial cylindrical recess 158 which is semi-circular in shape in top view. A not shown scanner ports through the surface defining recess 158 so as to read bar codes on labels of containers nested and then rotated within recess 158. Recess 158 is shown sized to receive a ten milliliter insulin vial. Recess 158 could be modified to include a smaller diameter, cylindrical recess, opening into the shown recess and arranged parallel therewith, for standard sized insulin cartridges. As shown in FIG. 11, partially projecting below recess 158 is stop member or platform 160 upon which vials can be placed or rested. Stop member 160 is horizontally extendable from the retracted position shown and includes a circular well 161 into which a vial fits when platform 160 is extended. Stop platform 160 alternatively may be fixed. Stop platform 160 and the not shown scanner are a fixed, vertical distance apart equal to the longitudinal distance between the bottom of a vial and the bar code mounted on the vial periphery. In operation, a user spins the vial inserted within recess 158 and positioned on platform 160 in order for the scanner to read the bar code and cause the internal componentry to generate an audible message as to the labeled contents.

Figure 12:
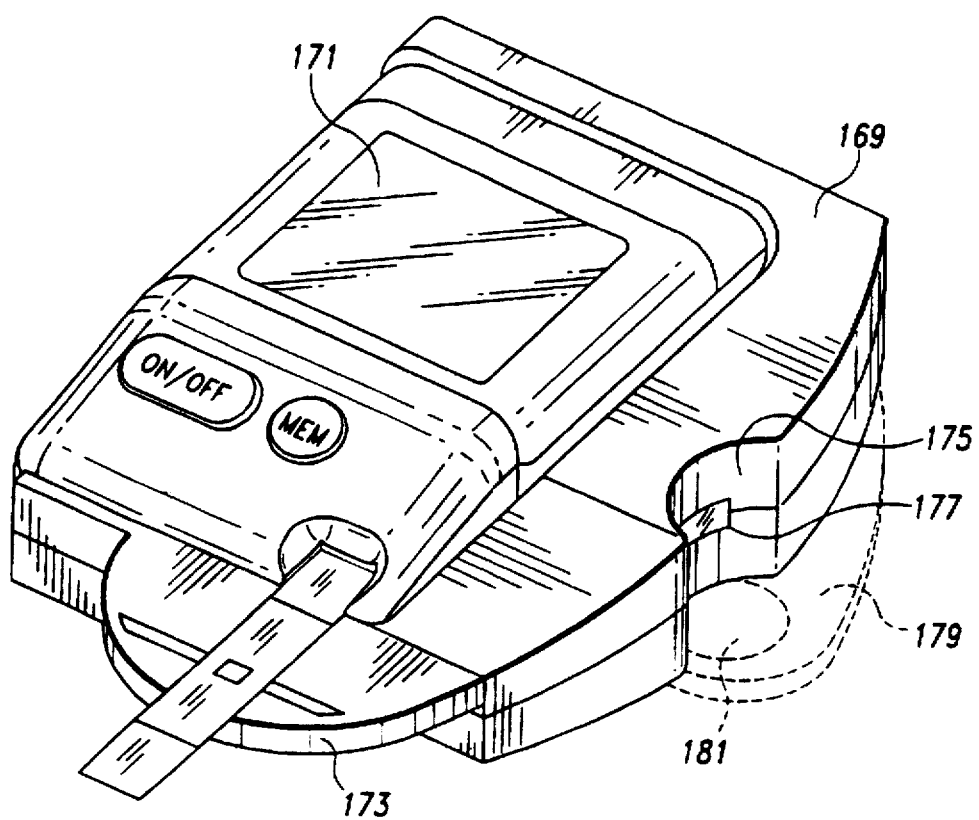
FIG. 12 is a front perspective view of a fifth embodiment of a blood glucose monitoring system of the present invention.

Referring now to FIG. 12, there is shown a fifth embodiment of a blood glucose monitoring system of the present invention. The system includes a base unit body 169 in which an Advantage™ type monitor 171 is maintained via detachable guide member 173. Along its side edge, base unit body 169 includes a cylindrical recess 175 in which an optical scanner 177 circuited to the base unit microcomputer is arranged. The base unit includes a platform 179 which pivots between a first position beneath the base unit body 169 and a second position, shown in dashed lines, laterally of the remainder of the base unit. The top surface of platform 179 includes a circular depression 181 into which the bottom end of an insulin vial inserts, and a user can use her hand to rotate the container within recess 175 to cause the container bar code to be read by scanner 177. The side of body 169 with recess 175 is rounded to facilitate one's hand in rotating the container.

Figure 13:
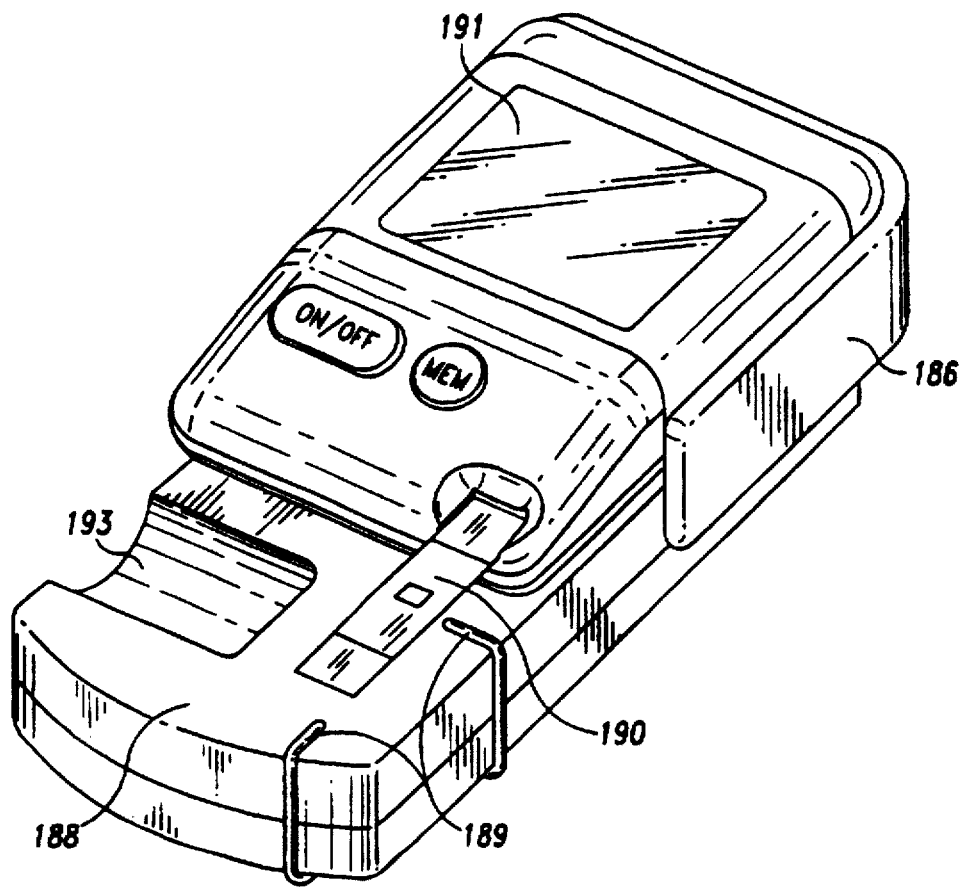
FIG. 13 is a front perspective view of a sixth embodiment of a blood glucose monitoring system of the present invention.

Referring now to FIG. 13, there is shown a front perspective view of a sixth embodiment of a blood glucose monitoring system of the present invention. This system includes a base unit body 186 including a portion 188 which forwardly projects beyond monitor 191. Ridges 189 in projecting portion 188 are provided for guiding test strip 190 into monitor 191 and then dosing test strip 190 with blood. Projecting portion 188 includes a horizontally aligned, cylindrical recess 193 shaped to receive the lower portion of an insulin vial arranged in a tipped over or sideways orientation. A not shown bar code reader ports into recess 193 to read the vial bar code.

Figure 14:
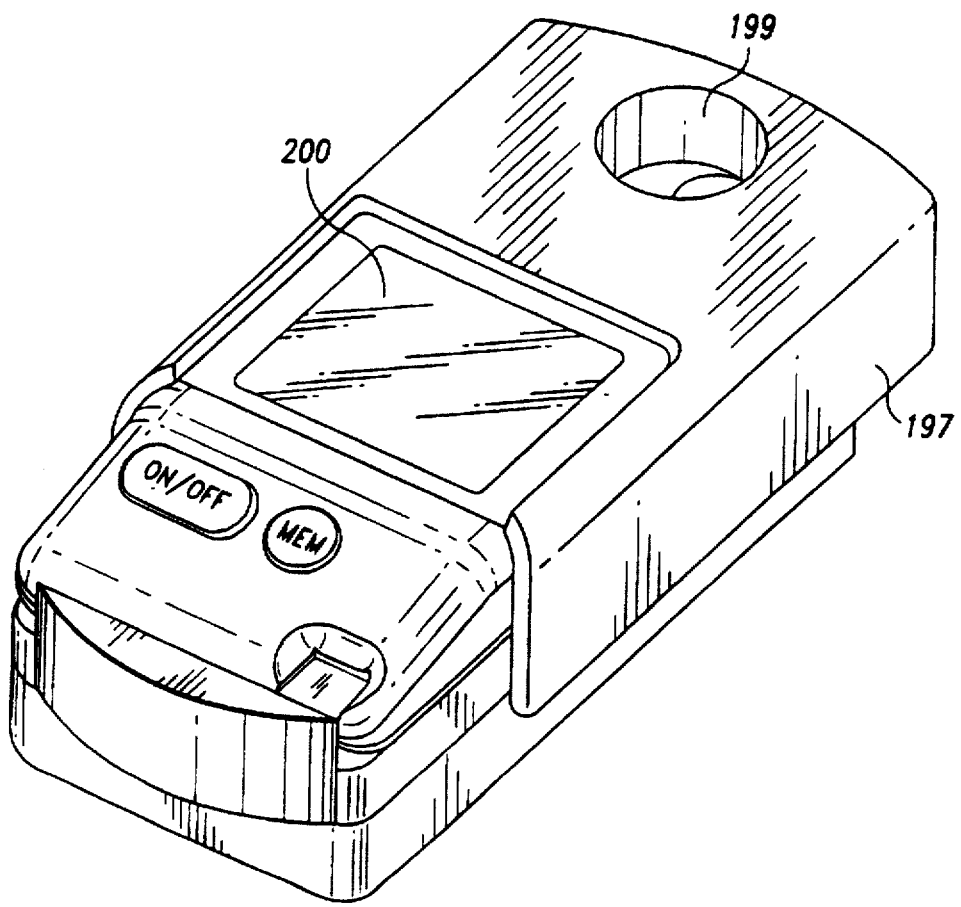
FIG. 14 is a front perspective view of a seventh embodiment of a blood glucose monitoring system of the present invention.

Referring now to FIG. 14, a seventh embodiment of a blood glucose monitoring system of the present invention is shown in which the recess 199 for accommodating insulin containers is centered within the base unit body 197 at a location rearward of the installed or assembled monitor 200. Although not fully shown, recess 199 includes first and second cylindrical recess portions with diameters particularly selected to separately accommodate vials and cartridges with bar codes read by a system scanner.

Figure 15:
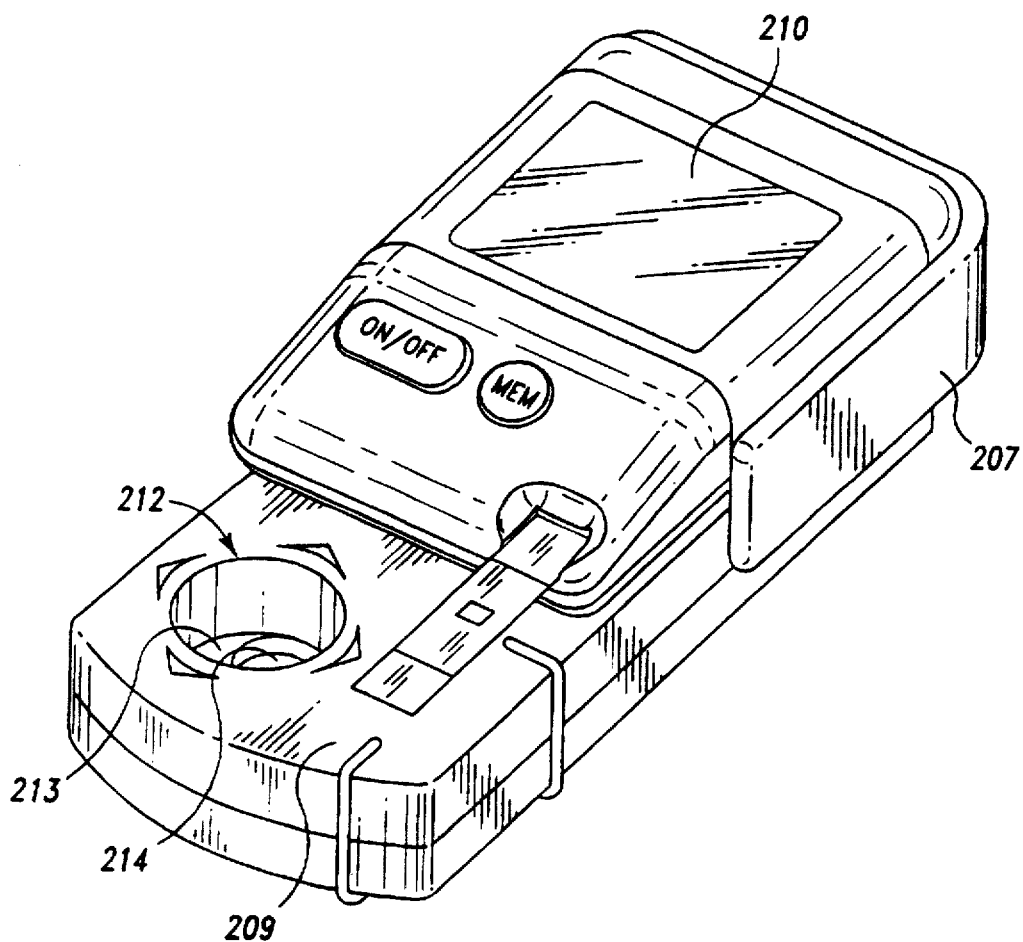
FIG. 15 is a front perspective view of an eighth embodiment of a blood glucose monitoring system of the present invention.
Figure 16:
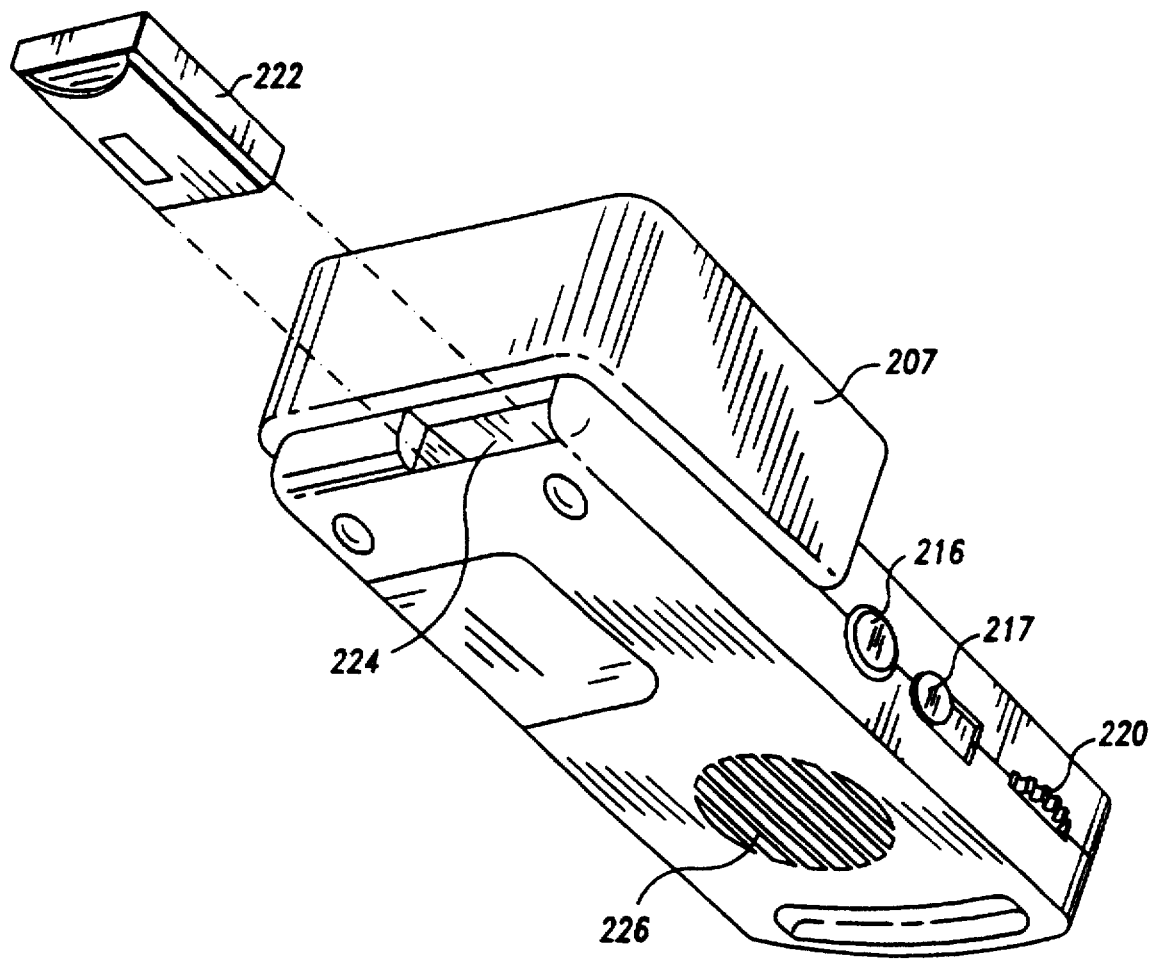
FIG. 16 is a rear perspective view of the system of FIG. 15.

Referring now to FIGS. 15 and 16, there is shown an eighth embodiment of the present invention. FIG. 15 is a front perspective view of the inventive embodiment, and FIG. 16 is a bottom, rear perspective view of the base unit without the blood glucose sensor and with a code key or chip shown removed from the base unit. Base unit body 207 includes a forwardly projecting portion 209 extending beyond the front face of monitor 210. Forward portion 209 includes a well-shaped recess 212 provided with a larger cylindrical recess 213 for vials and a smaller cylindrical and deeper cartridge recess 214. As is shown in FIG. 16, base unit body 207 includes a manually pressable repeat button 216, a male/female voice selection switch 217, and an on/off/volume dial 220. Code key 222 is shown removed from base unit body 207, and inserts into a not shown ROM key port circuited to the base unit microcomputer through opening 224. Speaker vents 226 are shown below an internal speaker through which speech output is broadcast.

Figure 17:
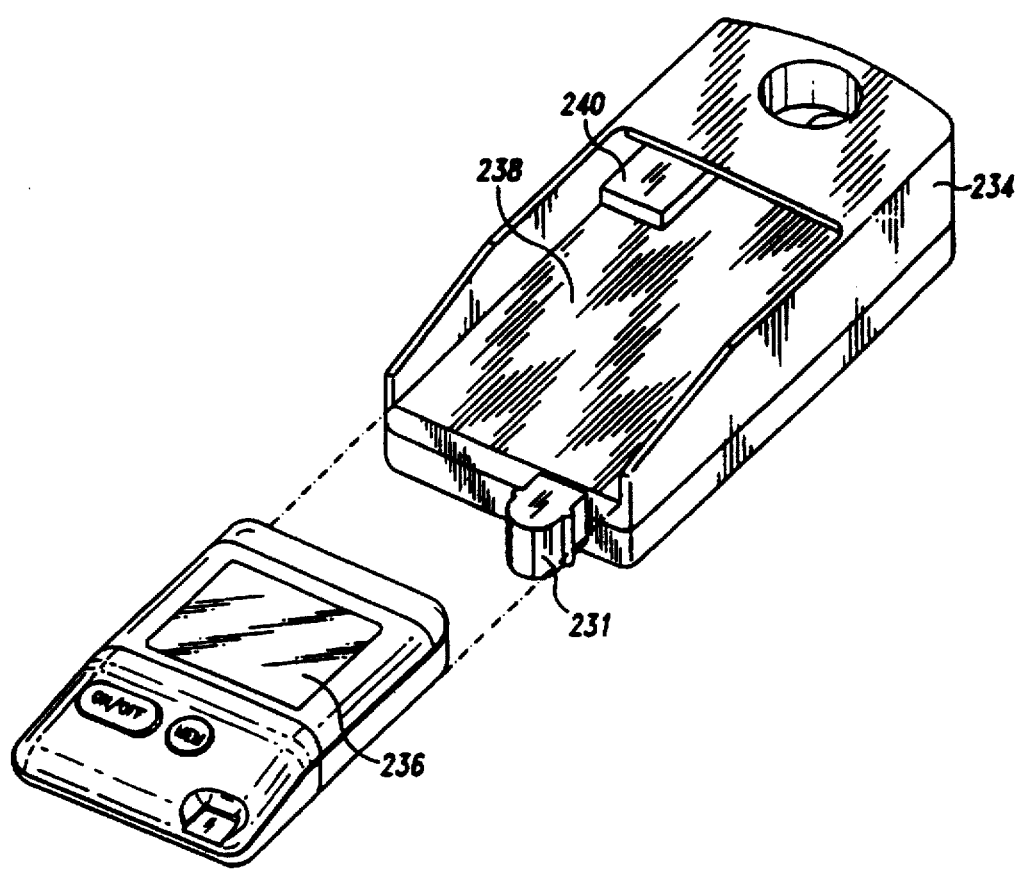
FIG. 17 is a front perspective view illustrating another embodiment of a system of the present invention.

Referring now to FIG. 17, there is shown still another alternate embodiment of a voice synthesizer or base unit. In this embodiment, guide member 231 is mounted to base unit body 234 and spring loaded to an upward monitor retaining position. In order to insert monitor 236, guide member 231 is manually pressed downward so monitor 236 may be slid into base unit body 234 to be seated on platform 238. As monitor 236 is so inserted, connector plug 240 inserts into the code key slot (not shown) of monitor 236 in order to provide an electrical interface between the monitor 236 and the base unit. When monitor 236 is inserted, guide member 231 automatically moves upward to an elevation abutting the monitor end to prevent monitor 236 from sliding forward in FIG. 17.

While this invention has been described and shown as having multiple designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A device for identifying a labeled content of a medication container comprising:
   a body including a portion shaped to accommodate the medication container;
   a reader arranged to read a medication identifying code on the container when the container is positioned at said body portion;
   a controller within said body and circuited to said reader to receive a signal from said reader corresponding to the read code, said controller comparing said signal to stored data;
   a voice synthesizer for generating a speech pattern identifying the medication in the container responsive to said controller comparing said signal and stored data; and
   a speaker for broadcasting the speech pattern to provide an audible message to a user of the device.

2. The device of claim 1 wherein said body portion is sized and configured to accommodate a vial.

3. The device of claim 1 wherein said body portion is sized and configured to accommodate a cartridge.

4. An insulin label reading device comprising:
   a body, said body either configured as an adaptor into which a separate portable blood glucose sensor removably inserts or configured as a housing into which a portable blood glucose sensor is integrated; means, within said body, for reading an insulin identifying code on an insulin container; and
   means, circuited to said code reading means, for providing an audible message to a user identifying a type of insulin labeled by the code as within the container.

5. The device of claim 4 wherein said code reading means comprises a recessed surface of said body sized and configured to insertably receive the insulin container.

6. The device of claim 5 wherein said code reading means further comprises a bar code reader porting into said recessed surface.

7. The device of claim 5 wherein said recessed surface defines a cylindrical well.

8. The device of claim 5 wherein said recessed surface comprises a partial cylindrical surface.

9. In a blood glucose monitoring system, a device for identifying a labeled type of insulin within a container comprising:
   a body including a portion shaped to accommodate an insulin container, said portion comprising a recessed surface;
   a reader arranged to read an insulin identifying code on the container when the container is positioned at said recessed surface;
   a controller within said body and circuited to said reader to receive a signal from said reader corresponding to the read code, said controller comparing said signal to stored data;
   a voice synthesizer for generating a speech pattern identifying the insulin in the container responsive to said controller comparing said signal and stored data; and
   a speaker for broadcasting the speech pattern to provide an audible message to a user of the device.

10. The device of claim 9 wherein said recessed surface defines a well-shaped concavity formed in said body.

11. The device of claim 10 wherein said well-shaped concavity is generally cylindrical.

12. The device of claim 10 wherein said well-shaped concavity comprises first and second concavity portions adapted for accommodating different sized insulin containers, wherein said second concavity portion longitudinally extends from said first concavity portion deeper into said body than said first concavity portion, and wherein said second concavity portion comprises a smaller transverse cross-sectional area than a transverse cross-sectional area of said first concavity portion.

13. The device of claim 9 wherein said recessed surface comprises a partial cylindrical surface.

14. The device of claim 9 wherein said body comprises a portable blood glucose sensor.

15. In combination:
   a medication container including a code arranged on a portion of an exterior container surface; and
   a device for identifying a labeled content of the medication container, said device comprising:
      a body including a portion complementarily shaped to said medication container;
      a code reader arranged to read said code on said container when said container is positioned at said portion;
      a controller within said body and circuited to said code reader to receive a signal from said code reader corresponding to the read code, said controller comparing said signal to stored data;
      a voice synthesizer for generating a speech pattern identifying the medication in said container responsive to said controller comparing said signal and stored data; and
      a speaker for broadcasting the speech pattern to provide an audible message to a user of the device.

16. The combination of claim 15 wherein said container comprises a cylindrical vial.

17. The combination of claim 15 wherein said container comprises a cylindrical cartridge.

18. The combination of claim 15 wherein said portion comprises first and second well-shaped concavities, said first well-shaped concavity adapted to receive a vial-type medication container, said second well-shaped concavity adapted to receive a cartridge-type medication container.

19. The combination of claim 15 wherein said container comprises a base, wherein said body portion comprises a stop element for engaging said container base, said stop element located at a first longitudinal distance from said code reader, and wherein said code is positioned on said container at a distance from said container base equal to said first longitudinal distance, whereby said code is longitudinally aligned with said code reader when said container is placed in said body portion.

* * * * *